(12) United States Patent
Corcoran et al.

(10) Patent No.: US 11,771,411 B2
(45) Date of Patent: Oct. 3, 2023

(54) PFO DEVICE

(71) Applicant: Encore Medical, Inc., Eagan, MN (US)

(72) Inventors: Michael Patrick Corcoran, Woodbury, MN (US); Joseph A. Marino, Apple Valley, MN (US); Englong Tan, Maplewood, MN (US)

(73) Assignee: Encore Medical, Inc., Eagan, MN (US)

( * ) Notice: Subject to any disclaimer, the term of this patent is extended or adjusted under 35 U.S.C. 154(b) by 0 days.

(21) Appl. No.: 17/558,898

(22) Filed: Dec. 22, 2021

(65) Prior Publication Data

US 2023/0190251 A1 Jun. 22, 2023

(51) Int. Cl.
*A61B 17/00* (2006.01)
*A61B 17/12* (2006.01)

(52) U.S. Cl.
CPC .... *A61B 17/0057* (2013.01); *A61B 17/12031* (2013.01); *A61B 17/12122* (2013.01); *A61B 17/12172* (2013.01); *A61B 2017/00243* (2013.01); *A61B 2017/00292* (2013.01); *A61B 2017/00597* (2013.01); *A61B 2017/00606* (2013.01); *A61B 2017/00623* (2013.01); *A61B 2017/00867* (2013.01)

(58) Field of Classification Search
CPC .......... A61B 17/0057; A61B 17/12031; A61B 17/12122; A61B 17/12172; A61B 2017/00243; A61B 2017/00292; A61B 2017/00597; A61B 2017/00606; A61B 2017/00623; A61B 2017/00867; A61B 17/00234; A61B 17/12022; A61B 2017/00592; A61B 2017/00575; A61B 17/12109; A61B 2090/3966; A61B 17/1214; A61B 2017/1107; A61B 2017/0649; A61B 17/12168; A61F 2/00

See application file for complete search history.

(56) References Cited

U.S. PATENT DOCUMENTS

| 10,743,852 | B2 | 8/2020 | Moszner | |
|---|---|---|---|---|
| 10,808,341 | B2 | 10/2020 | Köppe | |
| 2013/0218192 | A1* | 8/2013 | Erzberger | ........ A61B 17/12122 606/200 |

* cited by examiner

*Primary Examiner* — Katherine M Shi
*Assistant Examiner* — Nasheha Baset
(74) *Attorney, Agent, or Firm* — Forsgren Fisher McCalmont DeMarea Tysver LLP; James M. Urzedowski; Daniel A. Tysver

(57) ABSTRACT

A medical device for treating a PFO is presented as well as a mechanism for its delivery, repositioning and/or removal. The device includes a wire or cable framework of six shape-memory cables formed into a right side having six loops that support a right side sail and a left side having six loops that support a left side sail. The right side loops and left side loops are connected together via waist members that extend between the right side and left side loops. Each cable is threaded through a through hole of a central post and pass through one of each of four types of connecting collars that establish the basic shape of the PFO device and retain the cables together to form a flexible and resilient PFO device.

9 Claims, 12 Drawing Sheets

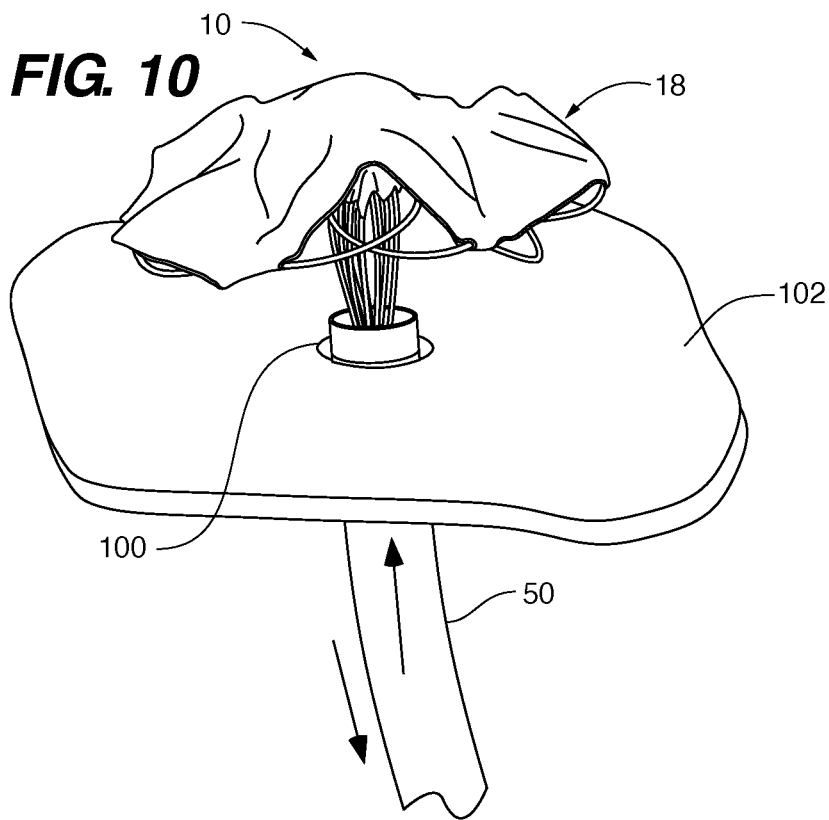
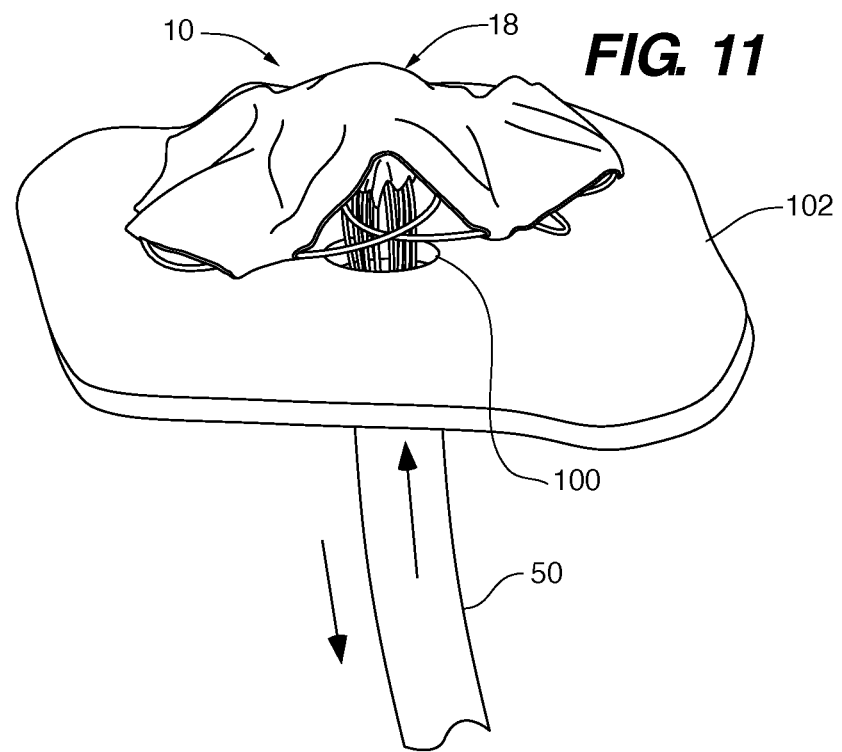

PFO DEVICE

FIELD OF THE INVENTION

Embodiments of the present disclosure relate generally to an occlusion device for closing an aperture in a biological structure and more particularly for closing a conduit or aperture in a heart wall, such as a defect between atrial chambers, as well as for methods and systems for deploying, repositioning and retrieving occlusion devices.

BACKGROUND OF THE INVENTION

The heart is comprised, generally, of four chambers: the left and right atria and the left and right ventricles. Separating the left and right sides of the heart are two walls or "septa". The septa are susceptible to a number of types of defects, including patent foramen ovale, atrial septal defects and ventricular septal defects. Although the causes and physical characteristics of these defects vary by type, they generally involve an opening (e.g. an aperture, slit, conduit, flap-covered aperture) through the septum that allows blood to shunt between chambers in the heart in an abnormal way that compromises the performance of the heart and circulatory system and has disadvantageous health consequences.

Normally, permanently repairing septal or other cardiac defects requires open heart surgery; a high risk, painful and costly procedure. In response to these concerns, modern occlusion devices have been developed to treat certain septal defects. Rather than surgery, these occlusion devices are small enough to be deployed by inserting a catheter into a major blood vessel and moving the occlusion device through the catheter. This type of procedure can be performed in a cardiac cathlab, and avoids much of the risks, cost, and pain associated with open heart surgery. Such occlusion devices can be used to treat a wide range of cardiac defects, including patent ductus arteriosus, patent foramen ovale (PFO), atrial septal defects, ventricular septal defects, and can be used to occlude other cardiac and non-cardiac apertures.

One type of occlusion device generally has a first side, which is positioned on one side of the defect, a second side, which is positioned on the opposite side of the defect, and a center section, which extends through the center of the defect. Since defect size varies from patient to patient, it is a challenge to center the center section within a particular defect, which is often essential to ensuring that the defect is optimally occluded. This is important because if the defect is not properly occluded, blood may continue to shunt through the defect lessening the effectiveness of the occlusion device. Known occlusion devices address the problem of variable centering in a variety of ways, such as for example through the use of articulated center posts or the use of flexible spring connector that extends between the sides, such as respectively described in U.S. 7,087,072, filed on Jan. 22, 2003; and U.S. Pat. No. 7,972,361, filed on Jun. 19, 2006; the entire contents of both of which are incorporated herein by reference.

Furthermore, many occlusion devices are designed so that the first and second sides are collapsible, allowing the occlusion device to fit inside a catheter. A catheter with a small diameter reduces trauma, improves maneuverability, and allows the occlusion device to be used in very young patients or in those who have a small vasculature. Therefore, it is desirable that the occlusion device be highly compact when in a collapsed position so that the smallest diameter catheter may be used for deployment.

Also, in the event the device is not optimally deployed initially, it is desirable that it is easily retrievable, so that the procedure may be performed again. While some types of occlusion devices are retrievable via catheter, many require open heart surgery to be retrieved. Even in instances where the occlusion device can be retrieved using a catheter, a different catheter with a larger diameter may be required for retrieval because the device may not readily resume the compact shape it had before deployment. Furthermore, once retrieved, the device may be compromised from the stress of withdrawing it back into the catheter, even if a larger diameter catheter has been used. As such, it may not be possible to reuse the retrieved occlusion device.

Thus, there is a need in the art for an occlusion device that is easily loaded into a catheter, and that can be retrieved, reloaded, and redeployed in situ. There is also a need in the art for an occlusion device which has a centering system to improve the ability of the device to be centered in the defect.

SUMMARY

Embodiments of a PFO device disclosed herein are comprised of six wire cables made from a super-elastic material that are threaded through a center post. Each of the six cables has ends that are mated together in a set of terminal connector collars. Each cable is routed and interleaved through additional groups of collars forming a set of loops. The loops are heat set to form a pair of opposed disk shapes whose loops support sail structures on each side of the device. It is the unique collar locations that control the shape of the loops.

This construction permits stresses imposed on the device to be shared across the device therefore reducing stress concentrations on either side of the device, and thereby making the device closely conform to the anatomy of the patient, thus improving performance of the device. The sail structure is continuous and completely covers the left side loops and is intermittent and interleaved on the right side. The center post is used for deployment and resides on the right side and the device is delivered through a catheter positioned in the right heart via a Seldinger or similar procedure.

When the PFO device is deployed through the PFO in the heart, the slightly smaller left sail resides in the left atrium and the slightly larger right sail is deployed in the right atrium. At least the left sail is provided with a low profile and smooth surface to minimize the chance of blood clot formation.

The PFO device is resiliently deformable through a range of positions from a collapsed, delivery shape that fits within a delivery catheter to an expanded, deployed configuration, with the wire loop supported sails radiating generally outward to sandwich tissue therebetween. The device is biased into the deployed configuration by way of the shape-memory material form which the wire loops are constructed. The distance between the frame-supported sails, as well as the various angles at which they may engage the opposed sides of the septum around the PFO is variable by way of the flexibility imparted to device by the wire construction.

These and other unique features provide for embodiments of the disclosure that provide PFO devices, which are highly adaptable for use in a variety of anatomies and which are resilient to the potential strains of loading, deployment and repositioning.

BRIEF DESCRIPTION OF THE DRAWINGS

FIGS. 8-13 are a series of side perspective views showing the deployment sequence for deploying the PFO illustrated in FIGS. 1-2 through a PFO of a septum of the heart via a delivery catheter.

DETAILED DESCRIPTION

Figure 1:
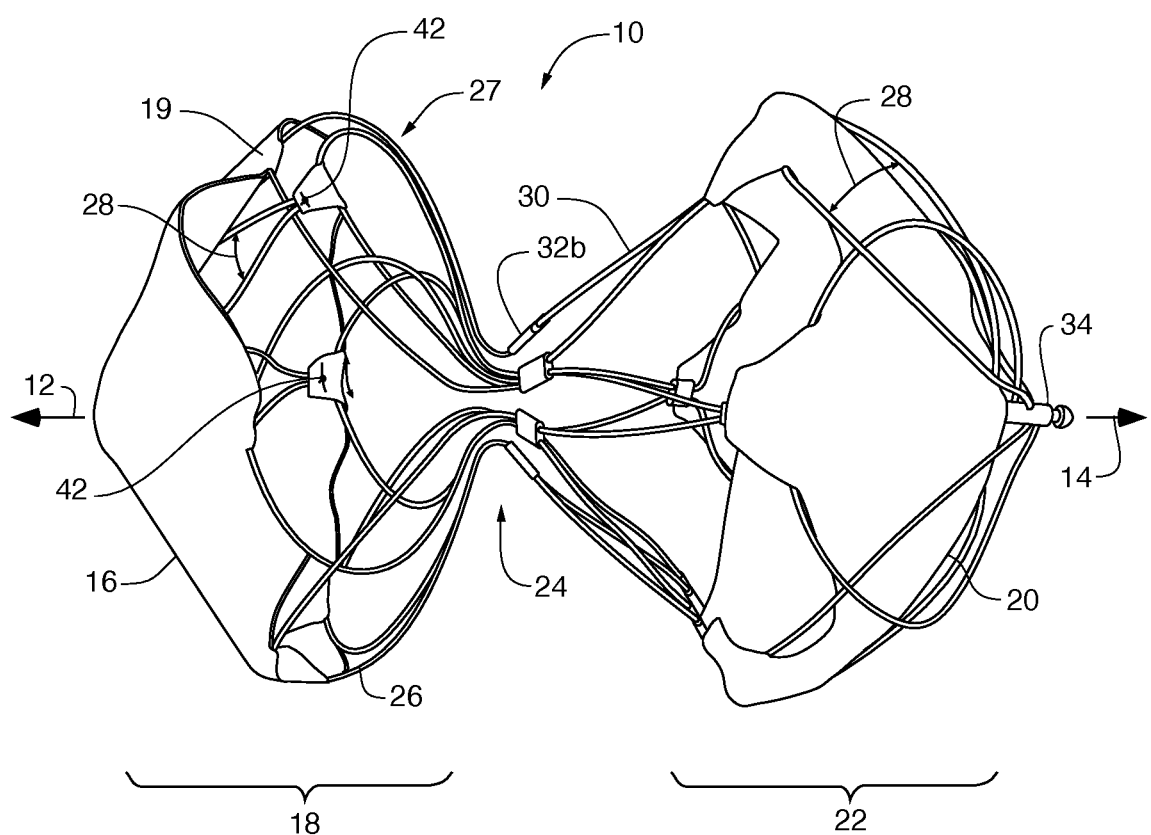
FIG. 1 is a side perspective view of an embodiment of a PFO device shown in stretched or slightly elongated state as if pulled in opposing longitudinal directions for illustrative purposes.
Figure 2:
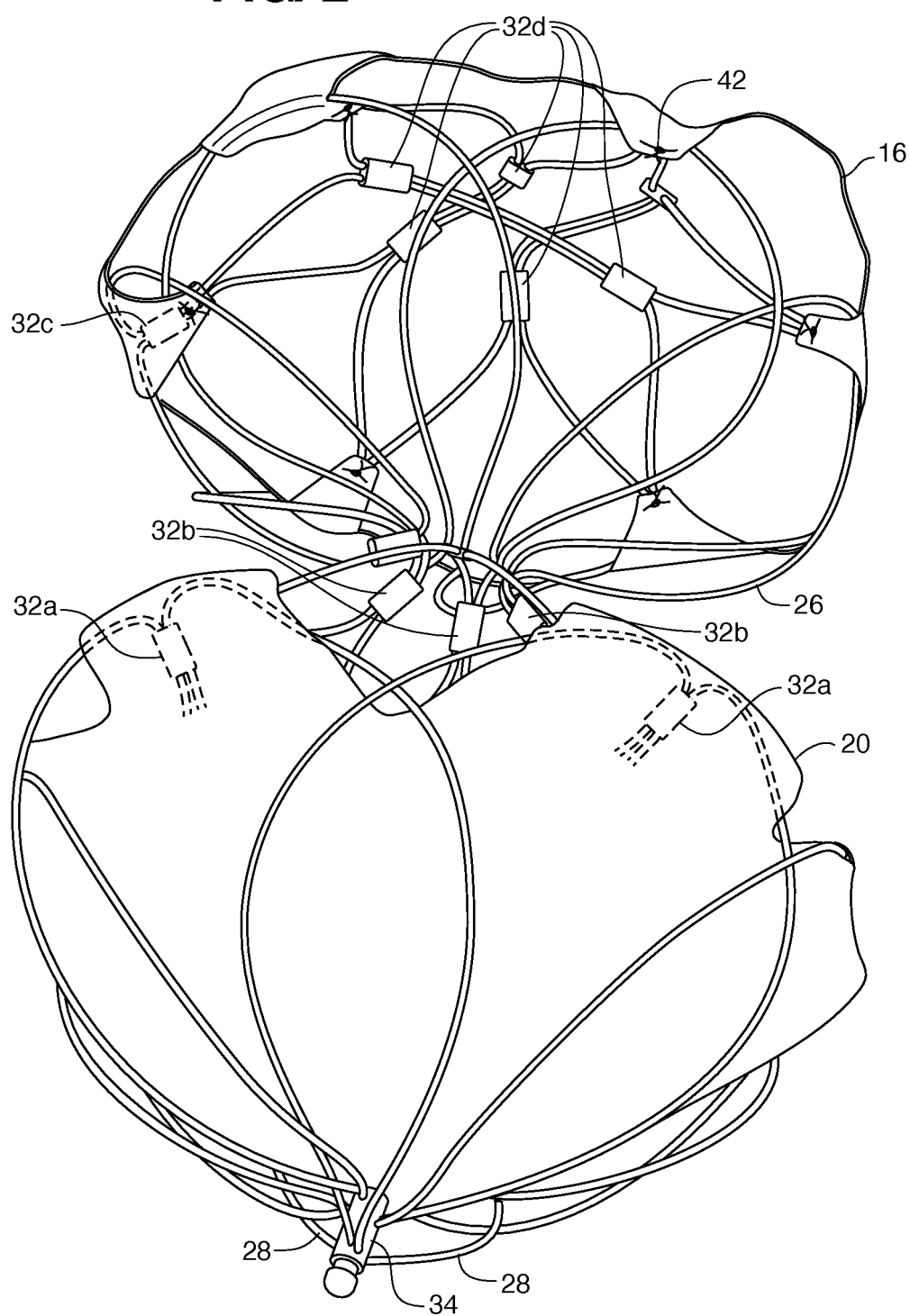
FIG. 2 is a proximal/right side perspective view of the embodiment shown in FIG. 1.

An exemplary embodiment of a PFO device 10 is shown in FIGS. 1 and 2. The device 10 is illustrated slightly stretched from its nominal shape by being pulled apart as indicated by force arrow 12 and force arrow 14. Seen in this stretched configuration there is a left sail 16 on the left side 18 and a right sail 20 on the right side 22.

Note that throughout, the terms "right" and "left" are used for convenient reference and are selected in accord with the orientation of the device as it would typically be situated in the heart and in accord with typical cardiac terminology for distinguishing the sides of the heart. These terms should not, however, be considered limiting.

Figure 13:
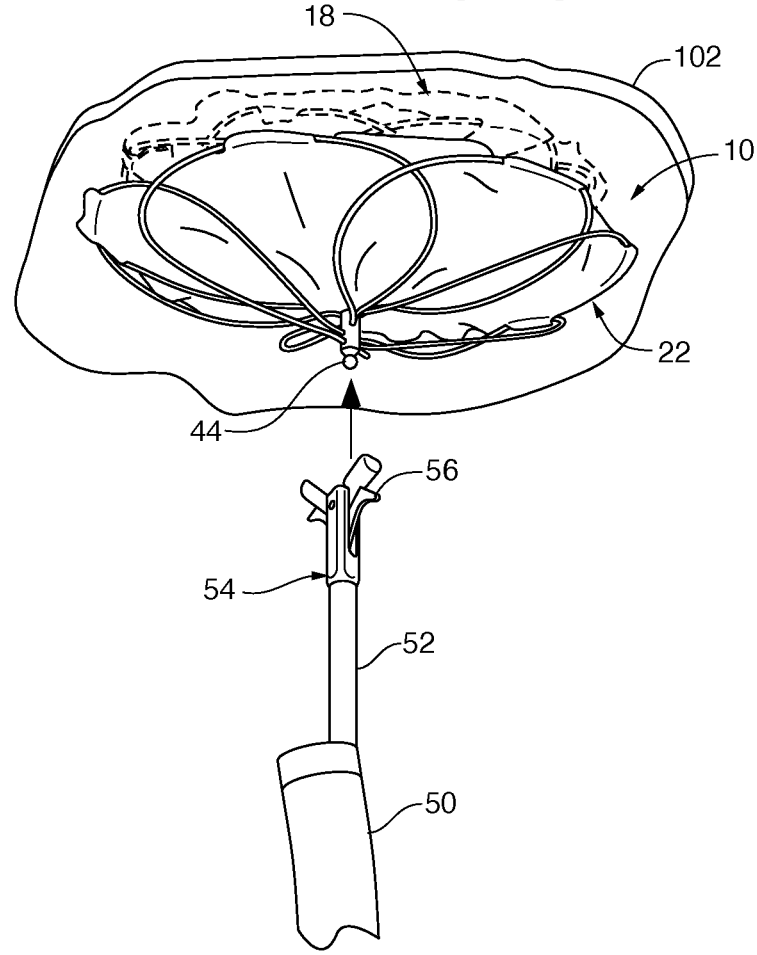
Figure 14:
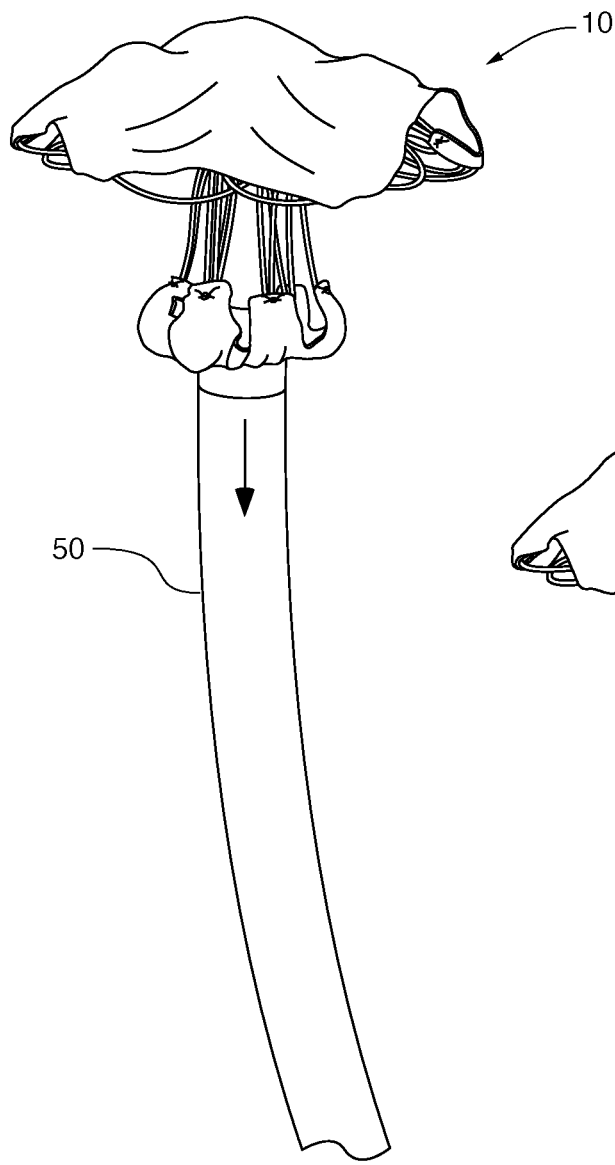
FIGS. 14-17 are a series of side perspective views showing the sequence for retracting the deployed PFO device shown in FIG. 13 back into a deployment catheter for removal or repositioning.
Figure 15:
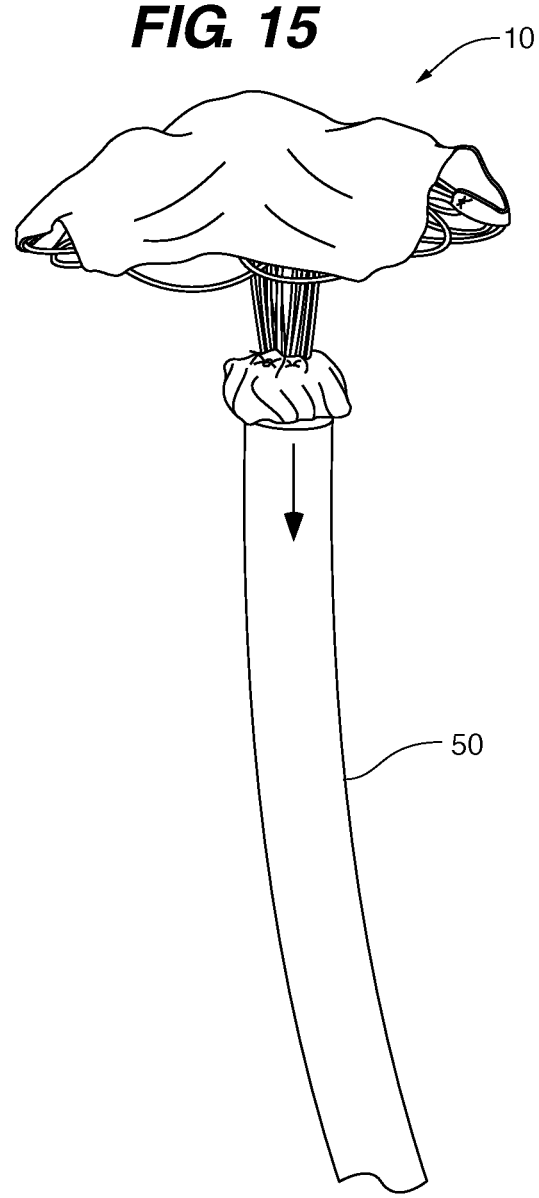
Figure 16:
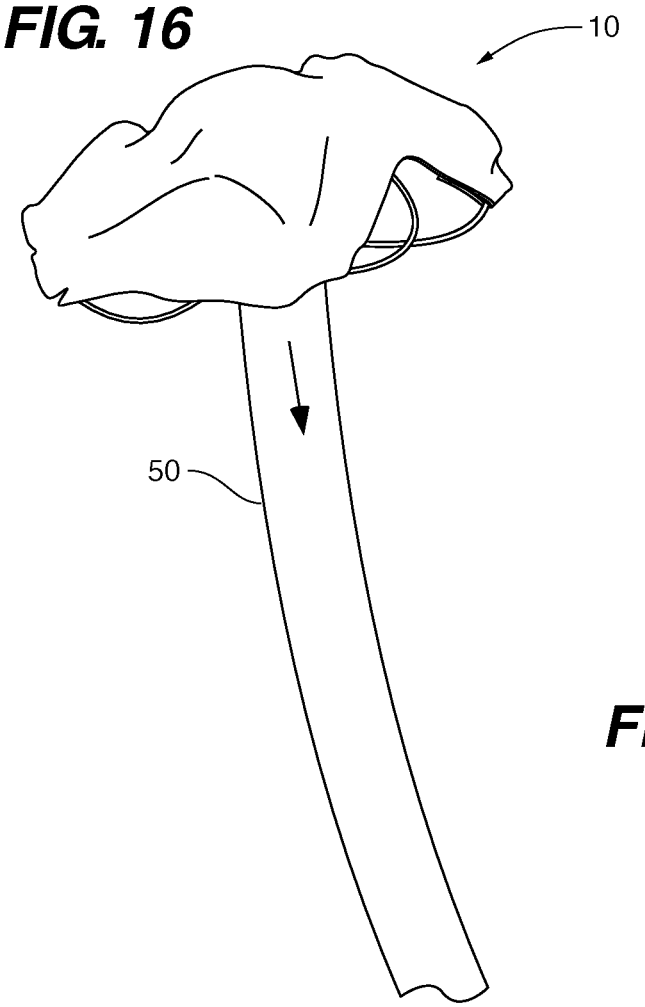
Figure 17:
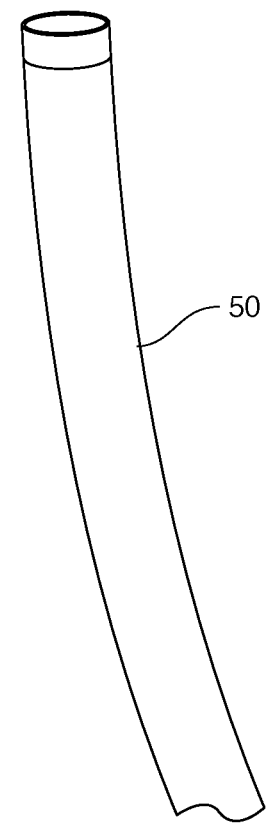

Device 10 includes a central waist region 24, which has a reduced diameter relative to the left side and right side sails 16 and 20, and is the portion of the device 10 which sits in the PFO 100 of the Septum 102 after deployment, such as in the manner shown in FIG. 13 (with the PFO 100 visible in FIGS. 8-11).

In the embodiment shown, the device 10, is made up of a series of wire cables 26. The cables 26 may be constructed of a single wire or stranded wire. In the embodiment shown, the PFO device is constructed of six cables 26. Cables 26 are preferably subjected to precise pre-shaping to give them a "shape memory" so that the PFO device 10 will be biased to maintain and resume after deployment from the confines of a delivery catheter. The pre-shaping can be done using any suitable method, such as machining, heat treating, or both.

In at least one embodiment, the cables 26 are at least partially constructed from multiple strands of one or more shape memory metals or alloys such as Nitinol. The cables 26 make up a framework 27 comprised of loops 28, which support the left sail 16 and right sail 20; and waist members 30 which extend from the loops 28 at either side 18 and 22 of the device to define the comparatively more narrow waist region 24.

The diameter of the cables 26 must be small enough so that the loops 28 which support the sails 16 and 20 are flexible enough to collapse when the device 10 is being loaded or retrieved. However, the cables 26 must be stiff enough to allow the loops 28 to lie as flat possible against the patient's septum with the waist members 30 biasing the loops 28 of the opposing sides 18 and 22 toward each other to create an effective seal against tissue of the septum around the PFO.

The precise shape of the loops 28 as well as the tendency for the waist members 30 to pull the sides 18 and 22 together is also provided by heat or machine shaping so that the loops 28 have shape memory to ensure that the loops 28 resume their proper deployed shape once the loops 28 leave the catheter such as in the manner shown in FIGS. 8-13.

Another advantage of pre-shaping the loops 28 using heat is to ensure that the loops 28 are properly sized. If the loops 28 are too large or too small for the device 10, the loops 28 may pucker or may cause the sails 16, 20 to pucker.

The programed shape and flexibility of the cables 26 allow the device 10 to have left and right sides 18, 22 which will not only tend to hug the tissue surrounding the PFO or other tissue opening or defect through which the device 10 is deployed (thereby creating a uniform seal around the opening), but also to reduce the potential for increased pressure on the surrounding tissue that might otherwise be caused by larger and/or stiffer structures such as are commonly used in some known devices. In the PFO device 10 shown, the support hoops 28 in combination with the waist members 30 help distribute pressure more evenly around a continuous circle, decreasing the possibility that increased pressure will be exerted at any one contact point. By distributing pressure more evenly, the risk that any part of one or more of the cables 26 will irritate or abrade septal tissue or is greatly reduced.

The sails 16, 20 are a mesh or woven fabric preferably formed of a medical grade polymer. In at least one embodiment the sails 16, 20 are at least partially constructed of Polyester. In at least one embodiment, the sails 16, 20 are at least partially constructed from a high density polyvinyl alcohol (PVA) foam, such as that offered under the trademark IVALON®. To minimize the chance of the device 10 causing a blood clot, the sails 16, 20 may be treated with a thrombosis-inhibiting material. One such suitable material is heparin.

In at least one embodiment the left sail 16 is a multilayer structure having a base layer 17 and external layer 19. The external layer 19 completely covers the loops 28 of the framework 27 with base layer 17 extending from the external layer 19 to secure the external layer 19 to the underlying left side 18 loops loops 28 via sutures 42.

Figure 7:
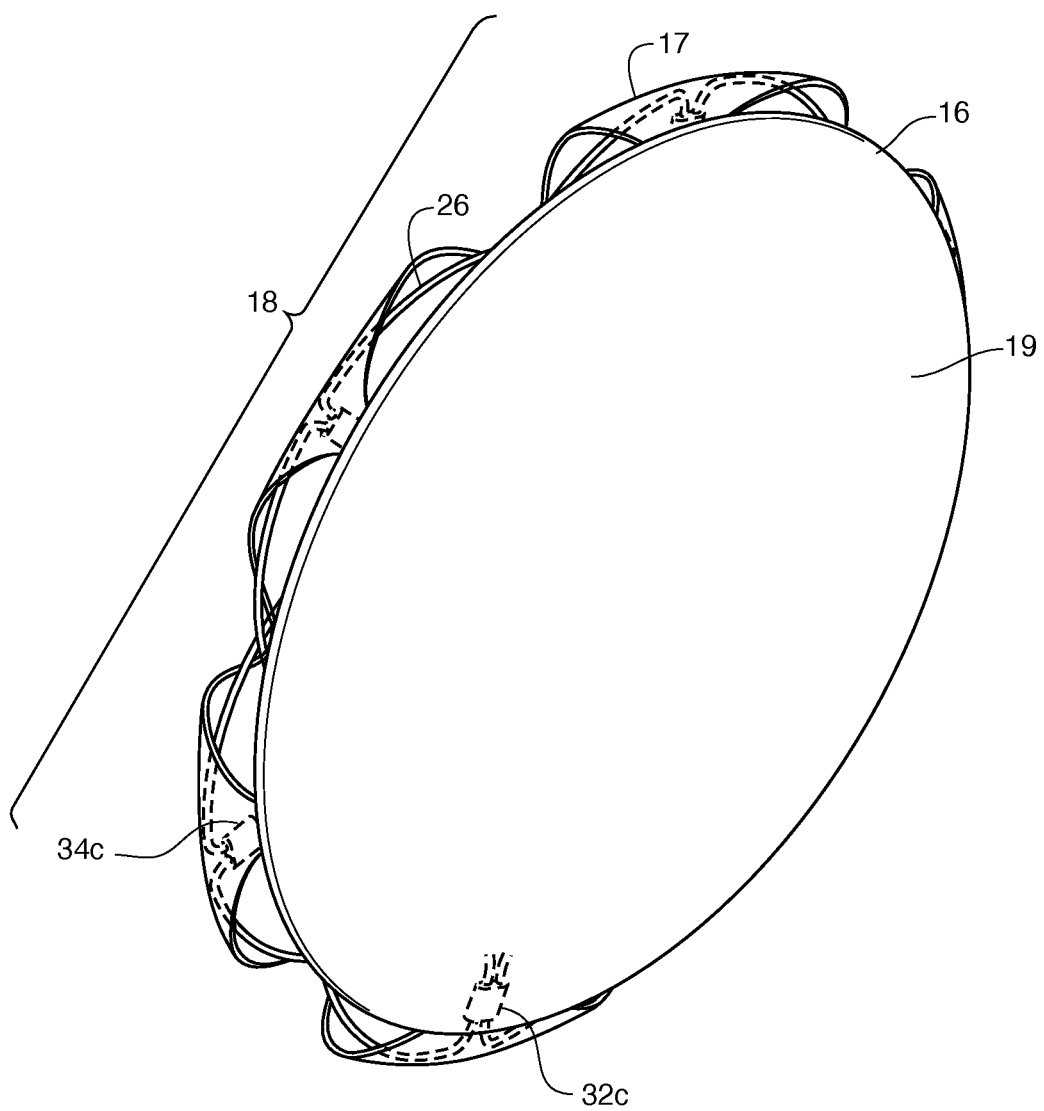
FIG. 7 is a distal/left side view of the PFO device shown in FIGS. 1-2, illustrating the left side sail.

In at least one embodiment, such as is shown in FIG. 7, the external layer 19 and base layer 17 is a single unitary piece of continuous medical grade polyester.

Figure 5:
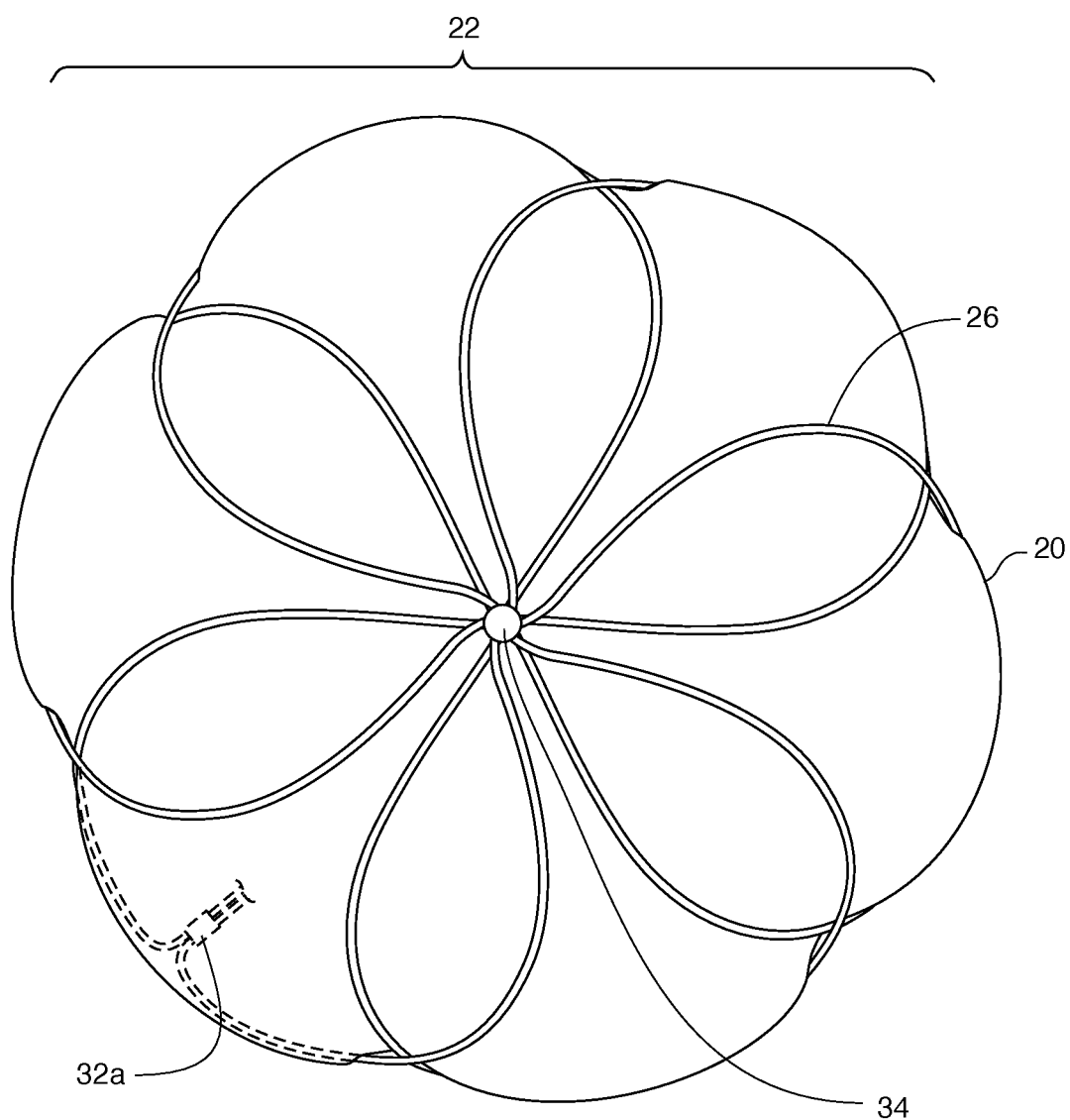
FIG. 5 is a proximal/right side view of the PFO device shown in FIGS. 1-2, illustrating the right side sail.
Figure 6:
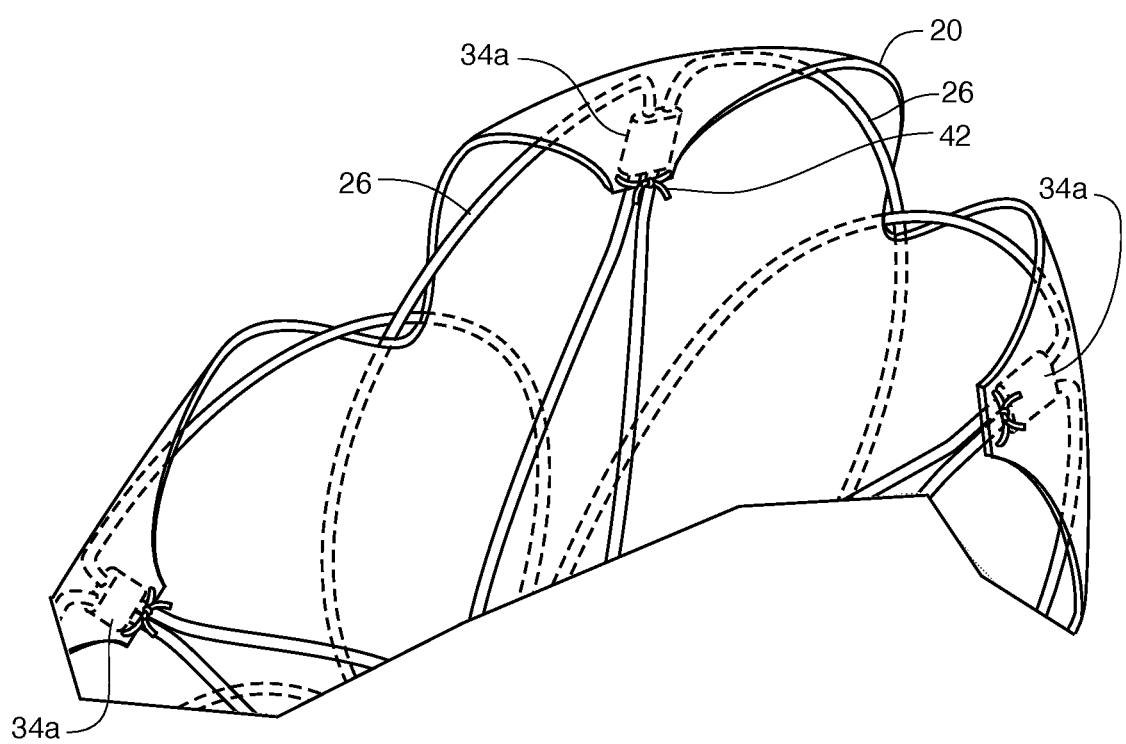
FIG. 6 is a partial, perspective view of the right side sail shown in FIG. 5, illustrating the group I collars used to form the sail's loops and provide securement areas for retention of the sail material.

In at least one embodiment, such as is shown in FIGS. 5-6 the right side sail 20 is interwoven between the cables 26 that make up the loops 28 on the right side 22.

Though the shape memory aspect of the cables 26 does provide the device 10 with its deployed state shape and the mechanical requirement to maintain that deployed state shape despite external distortion forced upon the device (such as by loading it into a catheter), the initial arrangement of the cables 26 relative to each other in order establish the basic configuration of the framework 27 is provided by a plurality of collars 32 and a central post 34.

In at least one embodiment, one or more of the collars 32 and/or the central post 34 is at least partially constructed of a radiopaque material or includes a radiopaque coating.

The central post 34 is provided with six through holes 36 (visible only in FIG. 4) through which each of the six cables 26 is passed therethrough. A plurality of four categories of collars 32a, 32b, 32c, and 32d connecting various regions of the six cables 26 to one another in order to form loops 28 and secure the ends 38 (visible in FIGS. 3-4) of the cables 26 together.

First group collars 32a form and hold the loops 28 of the right side 22 at the periphery of the sail 20. The manner in which of first group collars 32a are utilized is shown in FIGS. 5-6

Second group collars 32b connect adjacent waist members 30 at the central waist region 24 such as in the manner shown in FIGS. 1-2

Third group collars 32c connect adjacent cable extensions 38 (visible in FIGS. 3 and 4) on the left side 18 of the device 10, along the periphery of the left sail 16 such as in the manner shown in FIG. 7.

Fourth group collars 32d join the free ends 40 of the cable extensions within the framework interior such as in the manner shown in FIG. 2.

In at least one embodiment the PFO device 10 is comprised of a total of twenty four collars 32a, 32b, 32c, and 32d. As indicated above, each cable 26 passes though a single hole 36 in the central post 34. Each cable 26 is crimped in the central post and therefore anchored in the central post 34 forming extensions 38 extending from the opposed openings of the hole 36.

Figure 3:
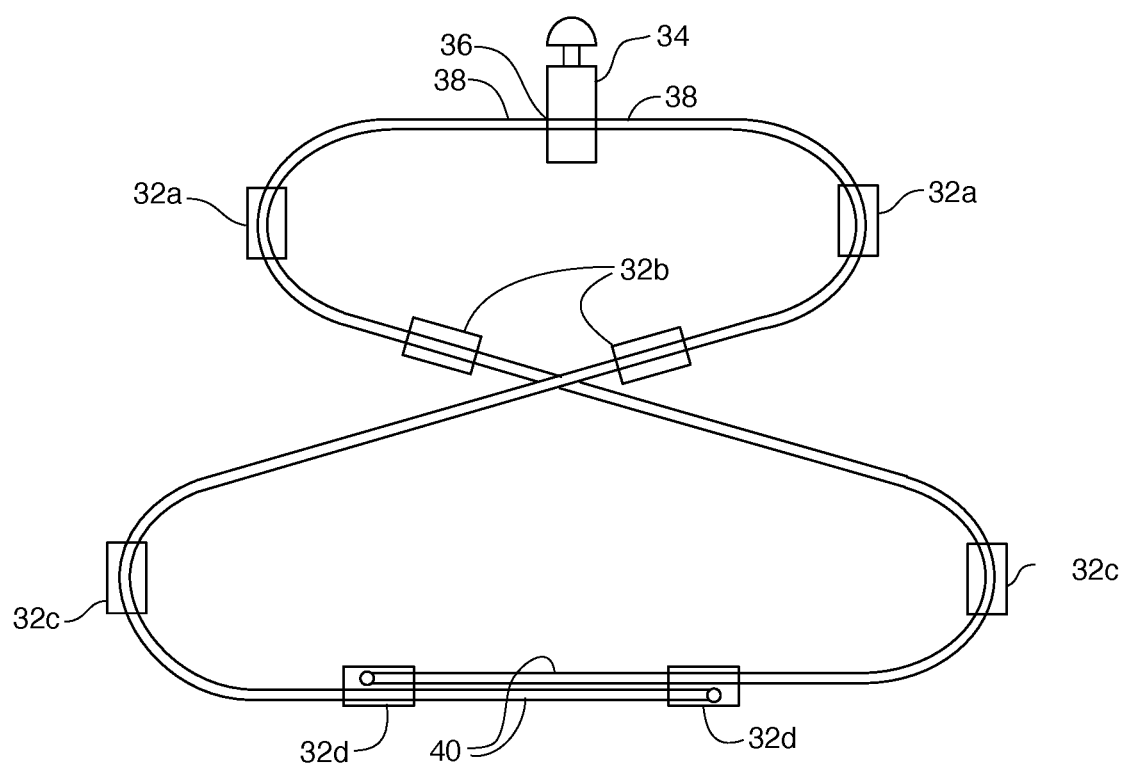
FIG. 3 is schematic diagram showing the distribution and arrangement of collars along a loop wire of the type shown in FIGS. 1-2.
Figure 4:
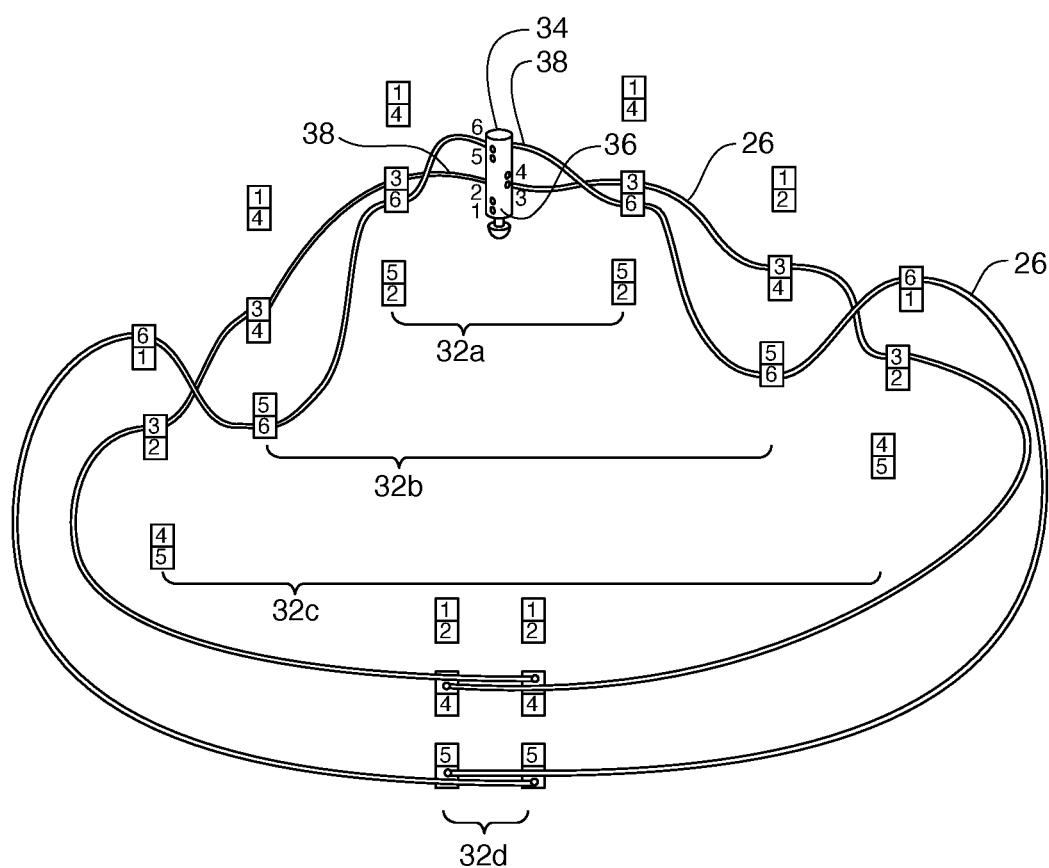
FIG. 4 is a schematic diagram illustrating part of the assembly process for making the PFO device shown in FIGS. 1-3.

To illustrate the manner in which the framework 27 is assembled, schematic illustrations of the manner in which a single cable 26 interacts with the central post 34 and the four types or regions of collars 32a, 32b, 32c, and 32d is shown in FIG. 3. In FIG. 4 two cables 26 are shown with the four classes of collar illustrated and the order of cables 26 which they engage based on their relative arrangement as dictated by the six holes 36 of the central post 34. Additional cables are added to the framework 27 in accordance with the pattern shown.

With reference to FIGS. 3-4, when the framework 27 is viewed as a whole such as in the manner shown in FIG. 2, it can be seen that each extension 38 of a cable 26 passes though one collar of each of the four groups 32a, 32b, 32c, and 32d, joining up with its complementary ends 40 at termination collar 32d. Thus, each individual cable 26 forms extensions 38 that is in turn formed in to a continuous member of the framework 27. The extensions 38 are interwoven through the collars 32a, 32b, 32c, and 32d to form twelve petals or loops 28. Six loops 28 support the fabric of the left sail 16 and six loops 28 support the fabric of the right sail 20. The fabric sails 16 and 20 are stitched to the cables 26, on the left and right side 18, 22 of the PFO device 10 via sutures 42.

In some embodiments, it may aid in securement of the respective left sail 16 and right sail 20, sutures 42 may be threaded through or simply biased against the collars 32c and 32a respectively.

As a result of this unique framework construction, forces are applied to the device 10 by heart motion are shared across the device from the left side and the right side. Unlike many previous PFO devices, the left and right sides 18 and 22 of the device 10 do not function independently but rather they are (and act as) a unitary structure sharing stress and spreading it over a large area which is beneficial.

As indicated above, the PFO device 10 may be used to address various openings or defects in tissue, and is especially suited for addressing the presence of a PFO in the septum of a mammalian heart. An exemplary procedure showing the delivery of the PFO device 10 from a catheter assembly 50 through a PFO or opening 100 of a septum 102 is shown in FIGS. 8-13.

Figure 8:
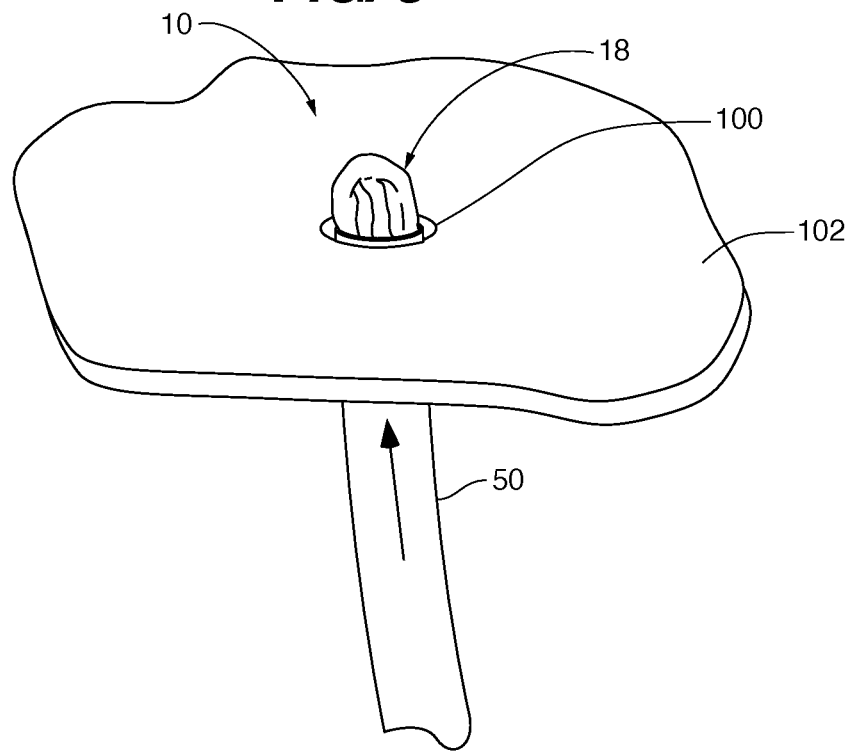

In FIG. 8 a catheter assembly 50 into which the PFO device 10 has been loaded in a compressed or unexpanded state is shown being advanced through the PFO 100 of the septum 102.

Figure 9:
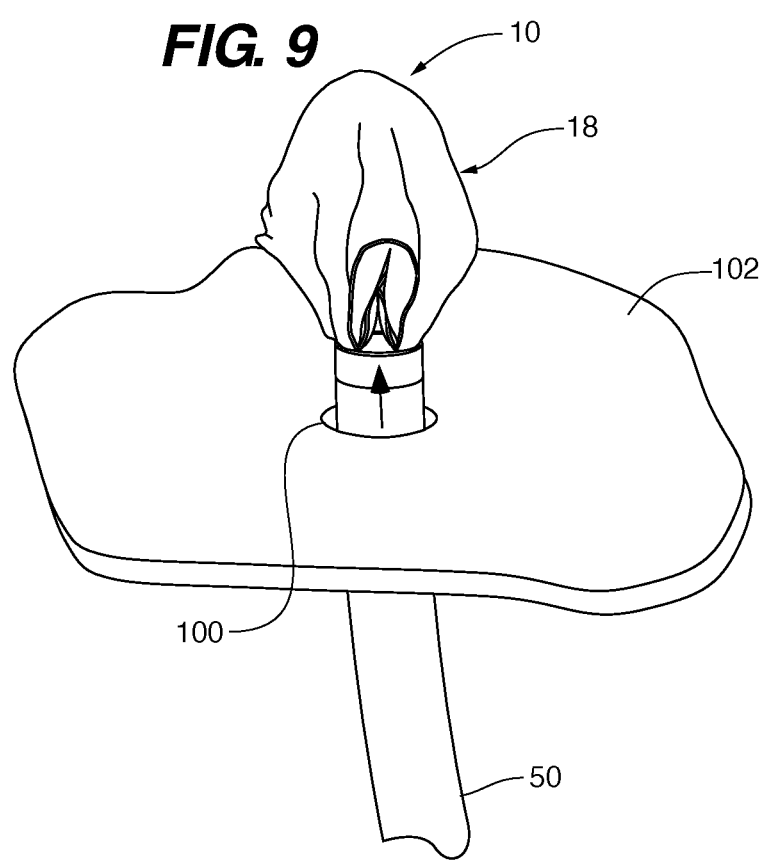

At FIG. 9, the PFO device 10 is advanced out of the catheter assembly 50 to allow the left side 18 of the PFO to self-expand.

At FIGS. 10 and 11 PFO device 10 continues to be advanced out of the catheter assembly 50 and self-expand. The catheter assembly 50 is pulled back to allow the expanded left side 18 of the PFO device to be seated against the septum 102.

Figure 12:
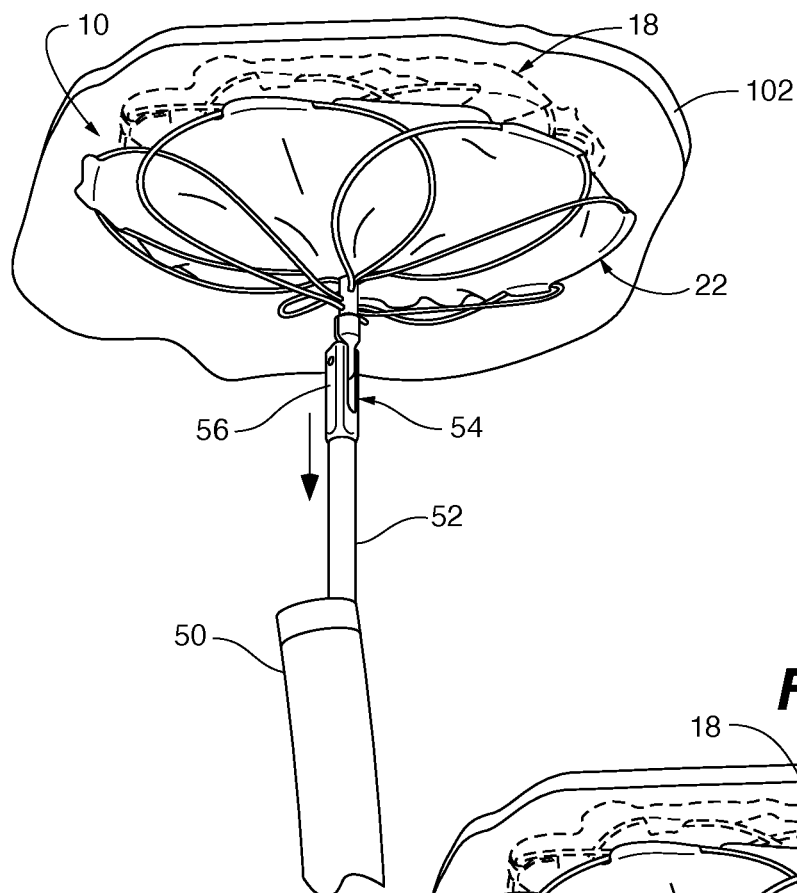

At FIG. 12 the delivery tool 52 and the catheter assembly 50 is shown. The delivery tool 52 is an elongated shaft that extends the length of the catheter assembly 50 and which incudes at its distal end 54 an actuatable retaining clamp 56 that is actuatable (via an actuation mechanism such as a button or trigger located at the proximal end of the tool (not shown)) between a closed position shown in FIG. 12 and an open position shown in FIG. 13.

The central post 34 includes a retaining knob 44 (visible in FIG. 13) which the retaining clamp 56 engages while the PFO device 10 during the delivery process.

The delivery tool 52 is movable relative to the catheter assembly 50 and by its advancement the PFO device 10 is advanced out of the catheter assembly 50 such as in the manner described above.

Once the left side 18 is seated against the septum 102 in the manner shown in FIGS. 10 and 11, the right side 22 is advanced out of the catheter assembly 50 and allowed to self-expand and seat against the septum 102 as well. While the PFO device 10 remains engaged to the delivery tool 52, the user may manipulate the tool 52 and the PFO device to assist in ensuring that the PFO device is properly positioned against the septum 102. Once properly positioned the PFO device 10 is released from the delivery tool by actuation and opening of the retaining clamp 56 such as in the manner shown in FIG. 13. Once the PFO device 10 is deployed the catheter assembly 50 is withdrawn from the patient.

In some cases, it may be necessary to reposition or remove the PFO device 10 from its original delivered position, such as is shown in FIG. 13. In that case, the catheter assembly 50 remains in place or is reintroduced as necessary. Once back in position adjacent to the deployed PFO device 10, the delivery tool 52 is advanced from the assembly 50 and recaptures the device 10 via actuation of the retaining clamp 56 onto the retaining knob 44.

Once the PFO device 10 is re-engaged by the delivery tool 52 (now functionally a capture tool), the PFO device 10 is pulled back into the catheter assembly 50 in the manner shown in FIGS. 14-17. Because of the extremely flexible nature of the framework 27 cables 26 and the device's programed shape memory, the PFO device 10 can by repeatedly compressed back into its unexpanded state within the confines of the catheter assembly 50, and re-delivered to the same or a new location as necessary without harming the structural integrity of the device.

The many features and advantages of the invention are apparent from the above description. Numerous modifications and variations will readily occur to those skilled in the art. Since such modifications are possible, the invention is not to be limited to the exact construction and operation illustrated and described. Rather, the present invention should be limited only by the following claims.

What is claimed is:

1. A self-expanding Patent Foramen Ovale (PFO) device having a confined state and an expanded state, and having a left side and a right side and a waist region therebetween, the device comprising:
   a central post, a plurality of cables, a plurality of collars, a left sail and a right sail,
   the central post being located on the right side, the central post defining a plurality of through holes, the plurality of through holes being equal to the plurality of cables, each of the plurality of cables passing through one of the plurality of through holes,
   each of the plurality of cables having a pair of ends,
   the left sail and the right sail each having a periphery,
   the plurality of collars being divided into a first group of collars, a second group of collars, a third group of collars, and a fourth group of collars,
   each of the plurality of cables passing through at least one collar of the first group of collars, at least one collar of the second group of collars, at least one collar of the third group of collars, and at least one collar of the fourth group of collars, to form six loops on the right side, six loops on the left side and six waist members extending between the six loops on the right side and the six loops on the left side;
   each collar of the first group of collars connecting two of the plurality of cables along the periphery of the right sail to form one of the six loops on the right side;
   each collar of the second group of collars connecting two of the plurality of cables at the waist region to form one of the six waist members;
   each collar of the third group of collars connecting two of the plurality of cables along the periphery of the left sail to form one of the six loops on the left side;
   each collar of the fourth group of collars connecting the pair of free ends of one of the plurality of cables.

2. The PFO device of claim 1, wherein in the confined state the device is configured to be folded into the interior of a catheter assembly.

3. The PFO device of claim 2, wherein the plurality of cables are constructed of a plurality of strands of shape memory material.

4. The PFO device of claim 3, wherein the shape memory material is nitinol.

5. The PFO device of claim 4, wherein at least one of the right sail and left sail are constructed of medical grade polyester.

6. The PFO device of claim 5, wherein the left sail completely covers the six loops on the left side.

7. The PFO device of claim 5, wherein the right sail is interwoven between the cables of the six loops on the right side.

8. The PFO device of claim 1, wherein the right side and left side have a diameter greater than the waist region.

9. The PFO device of claim 8, wherein the left side has a diameter less than the diameter of the right side.

* * * * *